United States Patent [19]
Carniglia et al.

[11] Patent Number: 5,391,550
[45] Date of Patent: * Feb. 21, 1995

[54] COMPOSITIONS OF MATTER AND METHODS FOR INCREASING INTRACELLULAR ATP LEVELS AND PHYSICAL PERFORMANCE LEVELS AND FOR INCREASING THE RATE OF WOUND REPAIR

[75] Inventors: Francis J. Carniglia, Windsor Locks; Alan J. Kenyon, Hartford, both of Conn.

[73] Assignee: Raymond A. Roncari, Windsor Locks, Conn.

[ * ] Notice: The portion of the term of this patent subsequent to May 8, 2007 has been disclaimed.

[21] Appl. No.: 416,248

[22] Filed: Oct. 2, 1989

Related U.S. Application Data

[63] Continuation-in-part of Ser. No. 139,288, Dec. 29, 1987, Pat. No. 4,871,718.

[51] Int. Cl.$^6$ .............................................. A61K 31/70
[52] U.S. Cl. ........................................ 514/23; 514/47; 514/48; 435/87; 435/88
[58] Field of Search ................ 514/974, 970, 23, 47, 514/48; 435/87, 88

[56] References Cited

U.S. PATENT DOCUMENTS

| | | | |
|---|---|---|---|
| 2,417,841 | 3/1947 | Ruskin | 514/47 |
| 2,844,514 | 7/1958 | Morrell et al. | 435/87 |
| 3,009,859 | 11/1961 | Laborit et al. | 514/47 |
| 3,104,203 | 9/1963 | Ruskin et al. | 514/47 |
| 3,157,635 | 11/1964 | Tanaka et al. | 536/28 |
| 3,298,923 | 1/1967 | Banno et al. | 435/88 |
| 3,329,567 | 7/1967 | Ruskin et al. | 514/26 |
| 3,686,392 | 8/1972 | Hamada et al. | 514/47 |
| 3,819,830 | 6/1974 | Yoshimura et al. | 514/47 |
| 3,823,234 | 7/1974 | Mauverney | 514/47 |
| 3,931,402 | 1/1976 | Ghielmetti et al. | 514/23 |
| 3,978,213 | 8/1976 | Lapinet et al. | 514/47 |
| 3,988,466 | 10/1976 | Takagi et al. | 514/561 |
| 4,046,879 | 9/1977 | Swetly | 514/47 |
| 4,078,971 | 3/1978 | Arkles et al. | 435/92 |
| 4,088,756 | 5/1978 | Voorhees | 514/47 |
| 4,126,701 | 11/1978 | Taylor | 514/641 |
| 4,207,315 | 6/1980 | Voorhees et al. | 514/47 |
| 4,211,770 | 7/1980 | Voorhees | 514/47 |
| 4,308,257 | 12/1981 | Caspe | 514/47 |
| 4,362,745 | 12/1982 | Johnston | 514/566 |
| 4,363,818 | 12/1982 | Gottlieb | 514/561 |
| 4,414,202 | 11/1983 | Silvetti | 514/561 |
| 4,427,650 | 1/1984 | Stroetmann | 424/46 |
| 4,546,095 | 10/1985 | Markov | 514/23 |
| 4,554,253 | 11/1985 | Imahori et al. | 435/288 |
| 4,575,498 | 3/1986 | Holmes et al. | 514/47 |
| 4,604,286 | 8/1986 | Kawajiri | 514/23 |
| 4,605,644 | 8/1986 | Foker | 514/23 |
| 4,764,375 | 8/1988 | Paradissis | 514/974 |
| 4,767,785 | 8/1988 | Georgieff | 514/561 |
| 4,772,591 | 9/1988 | Meisner | 514/23 |
| 4,871,718 | 10/1989 | Carniglia | 514/23 |
| 4,897,384 | 1/1990 | Janoff et al. | 536/17.9 |
| 4,916,161 | 4/1990 | Patall | 514/974 |
| 4,923,851 | 5/1990 | Carniglia | 514/23 |
| 4,945,087 | 7/1990 | Talwar et al. | 514/974 |
| 4,983,394 | 1/1991 | Hussein et al. | 514/974 |

FOREIGN PATENT DOCUMENTS

| | | |
|---|---|---|
| 046167 | 2/1982 | European Pat. Off. . |
| 047647 | 3/1982 | European Pat. Off. . |
| 148680 | 7/1985 | European Pat. Off. . |
| 150053 | 7/1985 | European Pat. Off. . |
| 8203552 | 10/1982 | WIPO . |

*Primary Examiner*—Ronald W. Griffin
*Attorney, Agent, or Firm*—Darby & Darby

[57] ABSTRACT

Disclosed are methods and compositions of matter for increasing the intracellular synthesis of ATP. The compositions comprise amino acids, metabolites, electrolyte and/or a pentose sugar. When applied to wounds, the invention increases the rate of wound repair and has a antimicrobial effect. When administered orally, the invention increases ATP blood levels and physical performance levels.

17 Claims, 13 Drawing Sheets

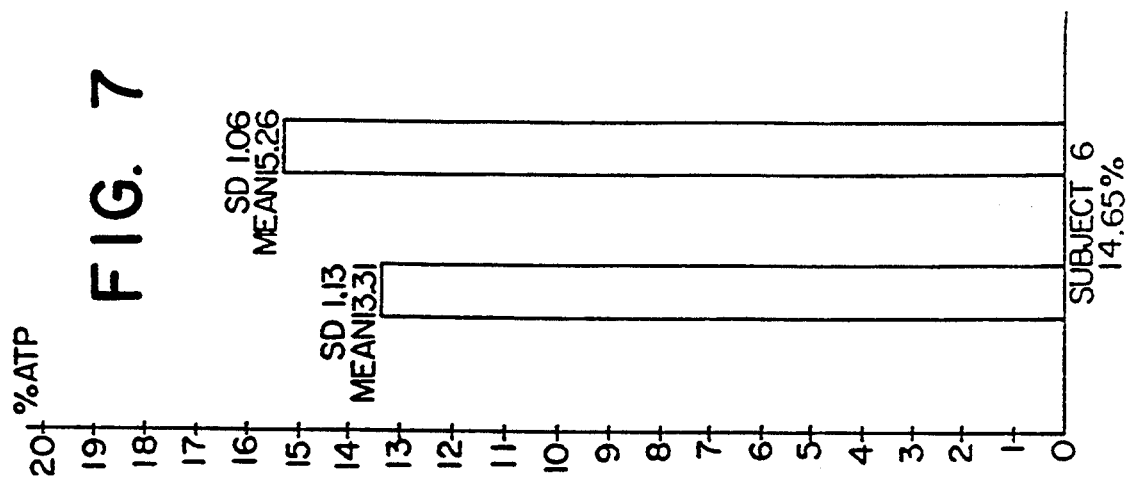
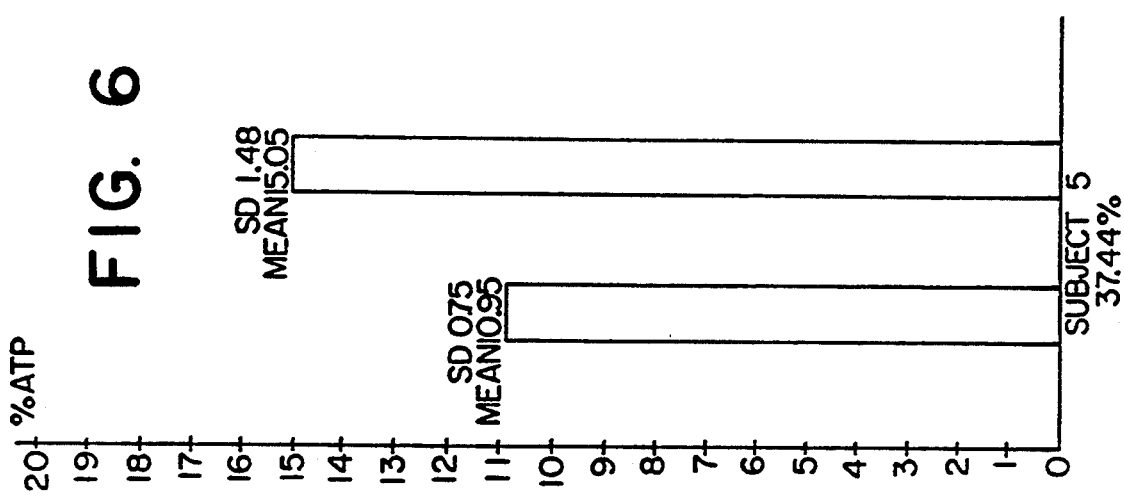
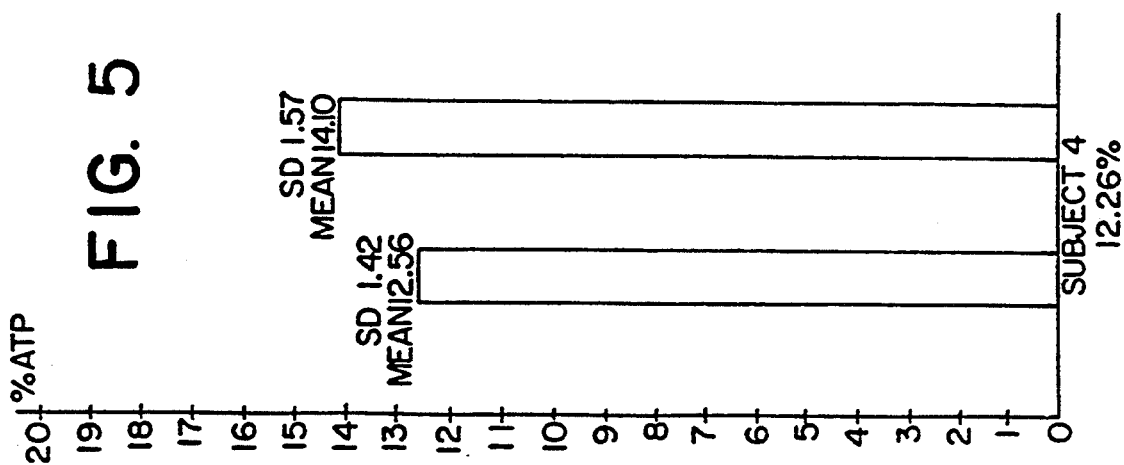

COMPOSITIONS OF MATTER AND METHODS FOR INCREASING INTRACELLULAR ATP LEVELS AND PHYSICAL PERFORMANCE LEVELS AND FOR INCREASING THE RATE OF WOUND REPAIR

This application is a continuation-in-part application of Ser. No. 07/139,288, filed Dec. 29, 1987, now issued as U.S. Pat. No. 4,871,718 on Oct. 3, 1989.

BACKGROUND OF THE INVENTION

1. Field of the Invention

One aspect of this invention relates to compositions of matter which provide the components required for increasing the intracellular synthesis of adenosine 5-triphosphate (hereinafter ATP) and to methods for increasing ATP levels in skeletal muscle cells. More particularly, the present invention relates to compositions and methods which increase ATP levels and physical performance levels when administered orally and to pharmaceutical preparations which increase the rate of wound repair and/or which have an antimicrobial effect when applied locally.

2. The Role of ATP in Cell Metabolism

The chemistry and biology of the adenine nucleotides began in 1847 with their isolation by Liebig (Liebig's ann 62: 317, 1847). At first these compounds were thought to be only degradation components of the nucleic acids; however, it was later realized that the chemistry and biology of the nucleotides derive from the purine bases adenine and hydroxanthine to which the five-carbon sugar d-ribose is added to form biologically active nucleoside precursors. The addition of phosphate to a nucleoside (purine base+pentose+phosphate) forms a nucleotide. By the early 1940's, attempts were being made to utilize the nucleotide ATP in the form of a Ca or Mg salt for energy enhancement.

ATP plays a diverse role in intermediary cell metabolism due to its high energy phosphate bonds. This was first demonstrated by Lipmann with regard to ATP's role in glycolysis (*Advances in Enzymology* 1, 99, 1947). Within the next four years, the central role ATP plays in respiration, carbohydrate metabolism, fat metabolism and the synthesis of urea and glutamine was clearly established.

Energy for muscular contraction and hence work comes from the hydrolysis of ATP. In skeletal muscle, ATP is hydrolized to adenosine diphosphate (hereinafter ADP) by the enzyme myosin ATPase. The hydrolysis of ATP to ADP is accompanied by the release of energy, and the process may be represented by the following reaction:

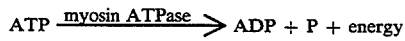

Muscular contraction proceeds for a few seconds during this liberation of energy.

ATP blood levels are only reported to decrease over short time periods. For example, ATP blood levels have been observed to drop in humans and horses during periods of highly intensive exercise. It is apparent that if contractile activity is to be maintained during such exercise, rapid synthesis of ATP must occur intracellularly (Hodgson, *Equine Practice*, Vet Clinics, December 1985).

There are two processes which provide intracellular replenishment of ATP: oxidative (aerobic) phosphorylation of substrates from circulating fatty acids and glucose and intramuscular glycogen and triglycerides; and, anaerobic phosphorylation in which ATP is generated from creatine phosphate, circulating glucose and glycogen stores.

In oxidative phosphorylation, muscle cells are unable directly to obtain ATP circulating in the blood; the reason appears to be associated with the binding of ATP's triphosphate component to the cell membrane. In most cells, the fewer the phosphates attached to the nucleotide, the more readily the nucleotide will be absorbed by the cell. Thus, cells will generally absorb adenosine monophosphate (hereinafter AMP) faster than ADP, and they will absorb ADP faster than ATP. AMP or ADP which has been absorbed by the cell must be rephosphorylated intracellularly to form ATP. This process involves the passage of hydrogen molecules from one step to the next along a reaction chain with the concurrent release of large amounts of chemical energy. Approximately half of this energy is utilized by the cell for further rephosphorylation of AMP or ADP, and the balance is given off as heat energy.

At the onset of exercise or under conditions where oxygen transport is insufficient, ATP stores built by oxidative phosphorylation become depleted; ATP, however, must still be made available to provide energy for muscular contraction. Anaerobic phosphorylation mechanisms are utilized by the muscle cells to provide the required ATP under these circumstances. Anaerobic phosphorylation occurs solely in the cell cytosol and mitochondria and involves high energy phosphates (phosgenes) represented by creatine phosphate (hereinafter CP), ADP and AMP.

The most important anaerobic phosphorylation mechanism appears to involve CP and may be represented as follows:

A second mechanism for restoring ATP levels in muscle cells is the myokinase reaction. Through this mechanism, muscle cells condense two molecules of ADP to form one molecule of ATP and one molecule of AMP. The mechanism may be represented as follows:

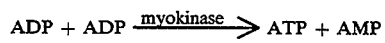

Substrate utilization through oxidative phosphorylation in, for example, exercising humans or animals such as racehorses, depends on the intensity of the work. ATP contributions through oxidative phosphorylation are directly related to the pace and speed of muscular contraction. As exercise continues, ATP becomes depleted and is restored by donations of energy from CP. When CP is depleted, other stores of energy are required. Although the myokinase reaction is present in skeletal muscle, it may have only a limited role in energy metabolism. Glycolysis and its end product pyruvate, which may be converted to lactate, provide the ongoing energy supply. In horses, the glycolytic process reaches peak efficiency approximately thirty seconds from the onset of exercise. Because equines have a large store of glycogen, this substrate is able to provide a considerable source of energy during exercise.

3. The Role of ATP in Wound Repair

The ATP dependency of the contractile mechanism in both striated and smooth muscle cells is signaled by the presence of divalent cations, particularly $Ca^{++}$ and $Mg^{++}$. It is significant that the content and function of calcium and magnesium in isolated myofibroblasts are analogous to their content and function in smooth muscle cells; hence, it appears that the contractile mechanism of the myofibroblasts is also dependent on ATP (*Science*, 1644–48, March 1987).

The myofibroblasts are a specialized population of fibroblasts; fibroblasts are connective tissue cells which, when differentiated, form binding and supporting connective tissue (e.g. collagen) such as tendons. The myofibroblasts are atypical fibroblasts which combine some of the ultrastructural features of fibroblasts and smooth muscle cells. The myofibroblasts have a dense collection of microfilament bundles that are rich in actin filaments. These bundles are muscle-like contractile fibrils.

A positive correlation has been established between the rate of wound repair in animals and the number of myofibroblasts present at the wound site. In many instances a wound lacks sufficient vascular development to support the nutritional needs of repair processes. This is so even when additional nutrients are provided by intravenous adminstration, since the primary means these nutrients have for reaching the repair site is by diffusion from the vascularized regions adjacent to the wound. An inadequate regenerative capacity of the host is particularly acute where the wound surface to be closed by granulation is large. In such instances, contraction of the wound surface, characterized by the movement of intact dermis over the wound site, plays an important role in the repair process by lessening the size of the wound gap (*J. Cenat.*, 89, 114–123, 1955). It is myofibroblasts, with their muscle-like contractile fibrils, which produce such wound contraction.

As noted above, the contractile mechanism of these fibrils is dependent on ATP. Thus, the rate of localized wound contraction produced by the myofibroblasts is dependent on the amount of ATP available to them as an intracellular energy source. Moreover, ATP serves as an energy source for other wound repair processes, including granulation of the wound by fibroblasts, gluconeogenesis and protein synthesis, and epithelialization.

Also important in the process of wound healing is the prevention or abatement of infection in a wound. Hence, antimicrobial agents have been recognized as important adjuvants to wound healing regimens.

In view of the diverse role ATP plays in cell metabolism and the importance of ATP to overall animal biochemistry and physiology, it is an aim of this invention to provide a method and composition of matter which supplies the components required for increasing the intracellular synthesis of ATP. It is also an aim of this invention to provide a method and composition of matter that exerts antimicrobial activity in a wound and thereby contributes to acceleration of the wound healing process.

SUMMARY OF THE INVENTION

In one aspect, the compositions of the present invention comprise amino acids, metabolites, electrolytes and a sugar, saccharide or polysaccharide that contributes ribose units to the synthesis of ATP when delivered to a cell. More specifically, the composition comprises amino acids selected from the group of amino acids which are the metabolic precursors of ATP and combinations of such amino acids. The compositions further comprise a metabolite, such as choline, carnitine or inositol, a pentose sugar, or a saccharide or polysaccharide (such as pentosan) which is, or upon hydrolysis or metabolization yields, d-ribose. The compositions also preferably comprise one or more electrolytes such as magnesium phosphate or preferably another source of soluble phosphate. The composition is formulated so that rapid absorption takes place without toxicity due to cell surface alteration.

It has been discovered that when the compositions of the present invention are administered orally, measurable to dramatic increases in intracellular ATP levels and physical performance levels result. Supporting data produced from seven equine case studies demonstrated that post-treatment ATP blood levels, a measure of intracellular ATP levels, increased a remarkable 23.5% on average following the oral administration of certain composition within the scope of the invention. Furthermore, a marked improvement occurred in measurable performance parameters and in more subjective evaluations.

It has further been discovered that when compositions according to the present invention are incorporated into a pyrogen-free vehicle and applied locally to a wound site, wound closure rate is increased. A composition of the present invention applied as a solution reduced wound size 17.8% faster than controls when applied once daily and 37.2% faster when applied three times daily. A single daily application of gel into which the present invention was incorporated reduced wound size 1.2% faster than control gels, whereas three applications daily reduced wound size 15.7% faster than control gels. Moreover, applications of compositions according to the invention also have an antimicrobial, i.e. an infection-preventing and/or infection abating effect.

BRIEF DESCRIPTION OF THE DRAWINGS

FIGS. 2–8 respectively illustrate mean ATP blood levels for each of seven individual subjects before and after dietary supplementation with the present invention.

DETAILED DESCRIPTION OF THE INVENTION

1. Increased Intracellular ATP Levels

Figure 1A:
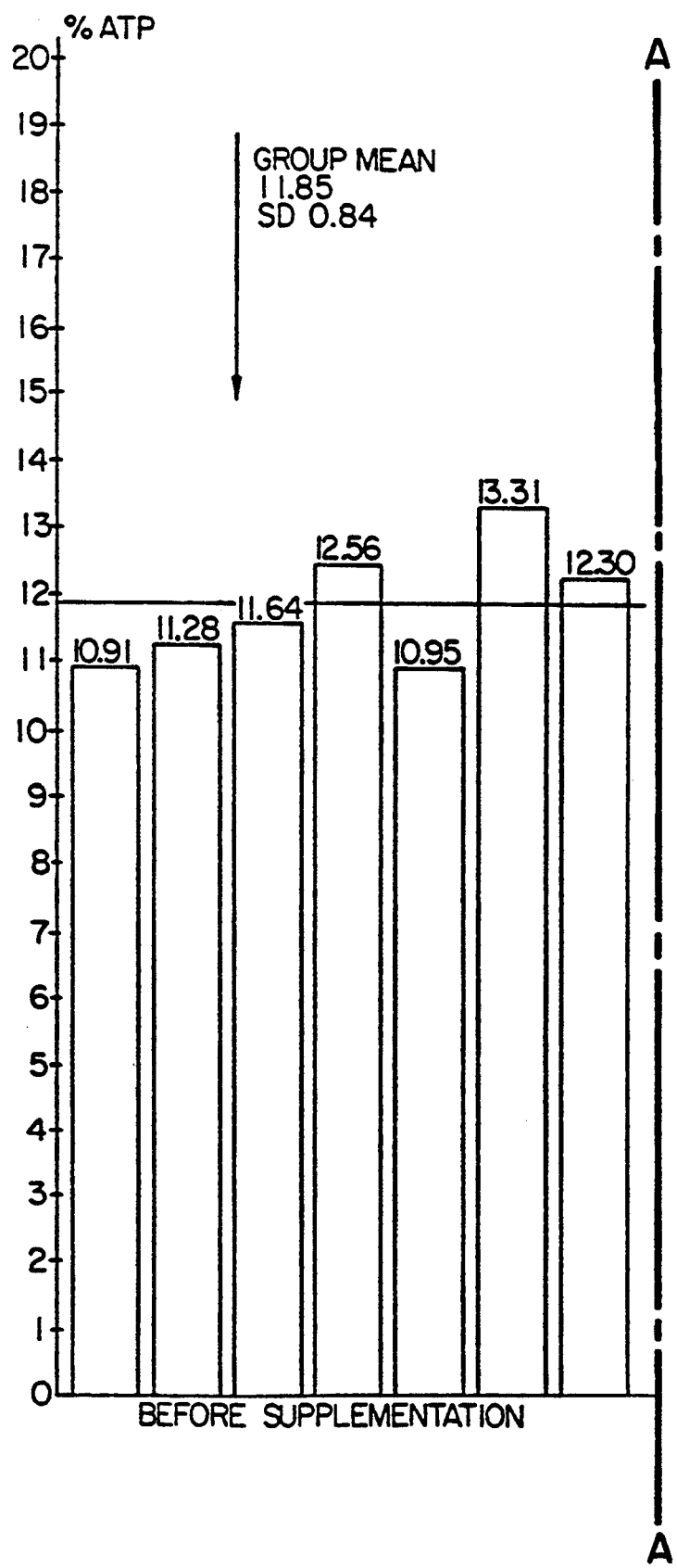
FIGS. 1A and 1B illustrate ATP blood levels and group mean levels for seven subjects whose diet was supplemented with the present invention.

It has been reported that profound adaptive response involving alterations in metabolic properties occur in the skeletal muscles of horses undergoing various forms of physical training. Dramatic increases in the concentration of mitochondria and concomitant increases in the concentration of oxidative enzymes involved in ATP production have been frequently documented. In contrast, the anaerobic potential of equine skeletal muscle is intrinsically high and is not greatly influenced by altered patterns of physical activity or nutrition. Accordingly, horses already involved in training programs, provide a particularly appropriate model for evaluating a composition designed to increase intracellular synthesis of ATP. Similarly, it is anticipated that compositions according to the present invention will increase ATP levels in human skeletal muscles and will improve physical performance in humans, most notably exercising humans, such as athletes and body builders who engage in anaerobic exercise.

To establish the efficacy of the present invention, seven Standard-bred horses already involved in training programs were selected. Each of the horses had hematological and blood chemistry studies performed prior to or at the outset of ATP baseline determinations. Blood samples were collected from each subject two to three times a week for a period of twenty-five days while the horses continued to receive their normal training ration of feed. Blood samples were drawn into ACD blood tubes (8.5 ml blood, 1.5 ml anti-coagulant); samples were held on ice until refrigerated at 4° C.

Whole blood was analyzed for levels of ATP within twenty-four hours after bleeding using the Sigma test kit procedure, Sigma Diagnostics, P.O. Box 14508, ST. Louis, Mo. 63178. In plasma, ATP is present in trace amounts at best. For this reason, ATP assay procedures require that blood cells be ruptured. Hence, the ATP level found in such an assay is directly related to the intracellular level of ATP. The procedure for ATP determination is based on the action of the enzyme phosphoglycerate phosphatase to form 1, 3 diphosphoglycerate from ATP and 3-phosphoglycerate. The enzyme glyceraldehyde phosphate dehydrogenase catalyzes the reaction to form glyceraldehyde-3-P and NAD+P, thus causing a reduction in the absorbance at 340 nm wavelength. The reaction, then is limited by the amount of ATP present, and the reduction in absorbance is proportional to the ATP present.

After the initial twenty-five day period, four of the subjects received eight ounces daily (4 oz. in A.M. feed, 4 oz. in P.M. feed) of a mixture containing the composition of the present invention and a group of nutritional elements. The nutritional elements were combined with the present invention primarily to make it more palatable to the horses and to provide additional vitamins and minerals. The most preferred composition of the present invention is set out in Table I along with the acceptable weight ranges of the individual components. Table II sets out the nutritional elements combined with the present invention in one preferred embodiment in their preferred weight ratios.

It should be appreciated that not all of the amino acids listed in Table I need to be present in a given composition in accordance with the invention. However, at least one amino acid which can be converted into ATP under intracellular conditions must be present. Also, only one of choline, (e.g. choline chloride, choline dehydrocholate or choline dihydrogen citrate) or inositol can be used, or they can be replaced by carnitine or mixtures of any two or any three of these metabolites can be used. Finally, an electrolyte should be present in the intracellular environment (whether administered as part of the present composition or not), preferably including a source of phosphate ion and most preferably also including a source of magnesium ion and/or manganese ion, such as potassium phosphate, and magnesium or manganese chloride. However, any physiologically acceptable source of phosphate and/or magnesium or manganese ion can be used, preferably a water-soluble salt thereof.

In a preferred embodiment, the present composition contains methionine (regardless of whether it also contains one or more other ATP precursor amino acids) and also preferably at least one of glycine, serine or retinol in amounts sufficient to suppress or counteract any toxic effect of methionine (elevated amounts of methionine in the blood stream are known to have toxic effects relating to fat mobilization in the liver as well as impediment of various other intracellular processes).

It should also be noted that either one of the ribose (or precursor) or metabolite need not form part of the composition of the present invention as long as they are present in the cells (through other means, such as separate ingestion of these ingredients by the mammal to be thus treated, or parenteral administration as is well-known) in amounts sufficient to produce increased levels of ATP. It is of course preferable that both the ribose (or precursors) and the metabolite form part of the composition of the present invention.

The amounts of the ingredients of the present invention are preferably as follows: about 30–60 parts amino acid, about 10–30 parts metabolite, and about 10–40 parts of ribose. The phosphate and magnesium (and/or manganese) containing electrolyte should be present in an amount at least sufficient to satisfy the phosphate requirement of ATP synthesis and to catalyze the ATP synthesis. Generally about 10–30 parts of magnesium phosphate can preferably be used. However, if separate sources of magnesium (or manganese) and phosphate are employed, the amounts of such sources can be readily determined to satisfy the phosphate demand and/or the magnesium (or manganese) demand based on the amount for magnesium phosphate given above. If excess methionine is used, up to 15 additional parts of methionine may be used. In that event, glycine, serine and/or retinol should also be used, preferably in amounts approximately equimolar to those of methionine.

TABLE I

| COMPONENT | PREFERRED | ACCEPTABLE |
| --- | --- | --- |
| L-glycine | 0.6 Kg | 0.5 Kg–0.7 Kg |
| L-arginine | 2.4 Kg | 2.2 Kg–2.6 Kg |
| D/L methionine | 12.0 Kg | 10.8 Kg–13.2 Kg |
| Choline chloride | 10.1 Kg | 9.1 Kg–11.1 Kg |
| Inositol | 8.9 Kg | 8.0 Kg–9.8 Kg |
| L-aspartic acid | 8.9 Kg | 8.0 Kg–9.8 Kg |
| L-tryptophan | 2.6 Kg | 2.3 Kg–2.9 Kg |
| L-phenylalanine | 2.1 Kg | 1.9 Kg–2.3 Kg |
| L-histidine | 2.0 Kg | 1.8 Kg–2.2 Kg |
| L-proline | 1.5 Kg | 1.4 Kg–1.7 Kg |
| D-ribose | 8.9 Kg | 8.0 Kg–9.8 Kg |
| Magnesium phosphate | 7.7 Kg | 6.9 Kg–8.5 Kg |
| Total | 67.7 Kg | 60.9 Kg–74.6 Kg |

TABLE II

| COMPONENT | AMOUNT |
| --- | --- |
| Lactalbumin | 300.00 Kg |
| Diamond V-Yeast Culture | 340.90 Kg |
| Dried Beet Molasses | 181.80 Kg |

TABLE II-continued

| COMPONENT | AMOUNT |
| --- | --- |
| Dicalcium phosphate | 90.90 Kg |
| Sodium bicarbonate | 22.70 Kg |
| Vitamin Premix | 45.45 Kg |
| Lignan sulphate | 13.07 Kg |
| Flavoring agents | 1.36 Kg |
| Total | 996.18 Kg |

Background information for each horse was collected regarding training performance, stamina, race times and results, and general history. A daily journal was maintained by the trainer for each horse during the study period.

Figure 1B:
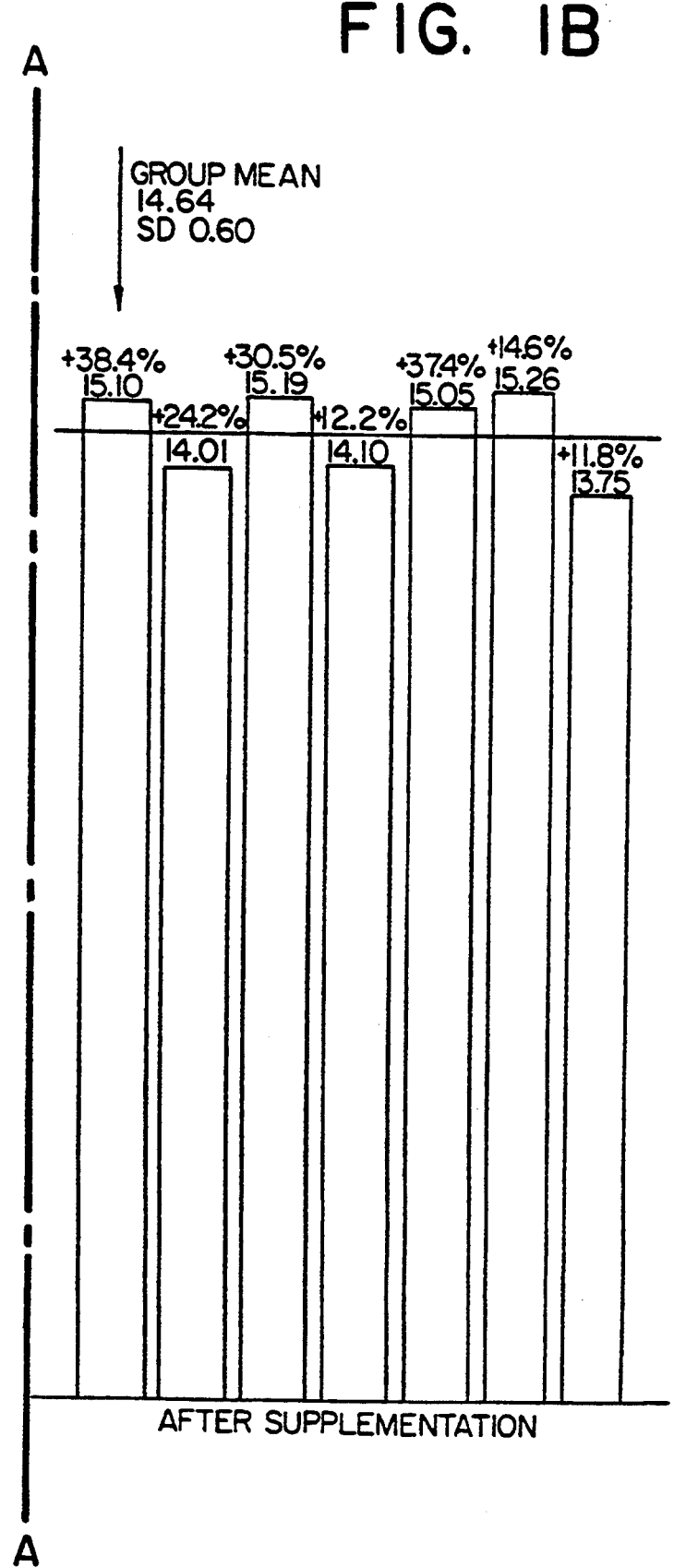
Figure 2:
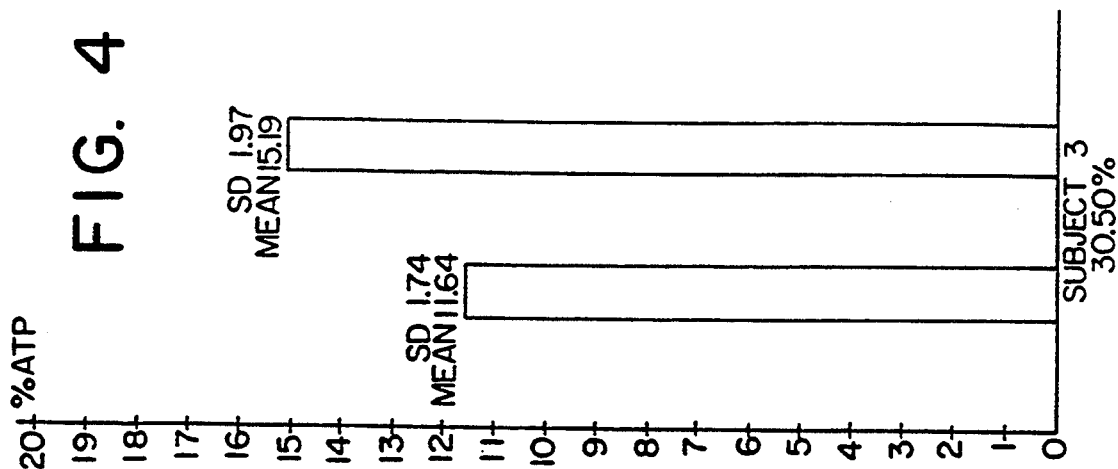
Figure 3:
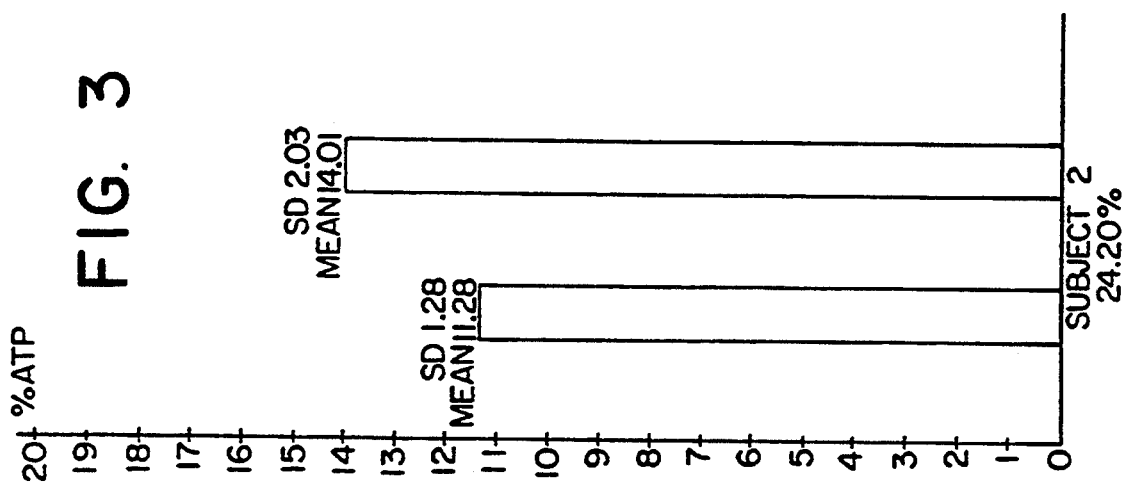
Figure 4:
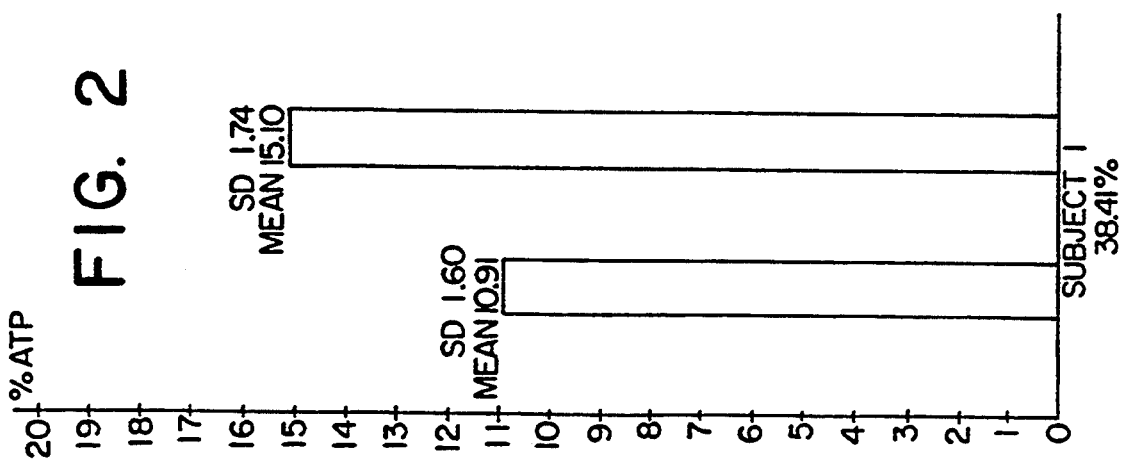
Figure 8:
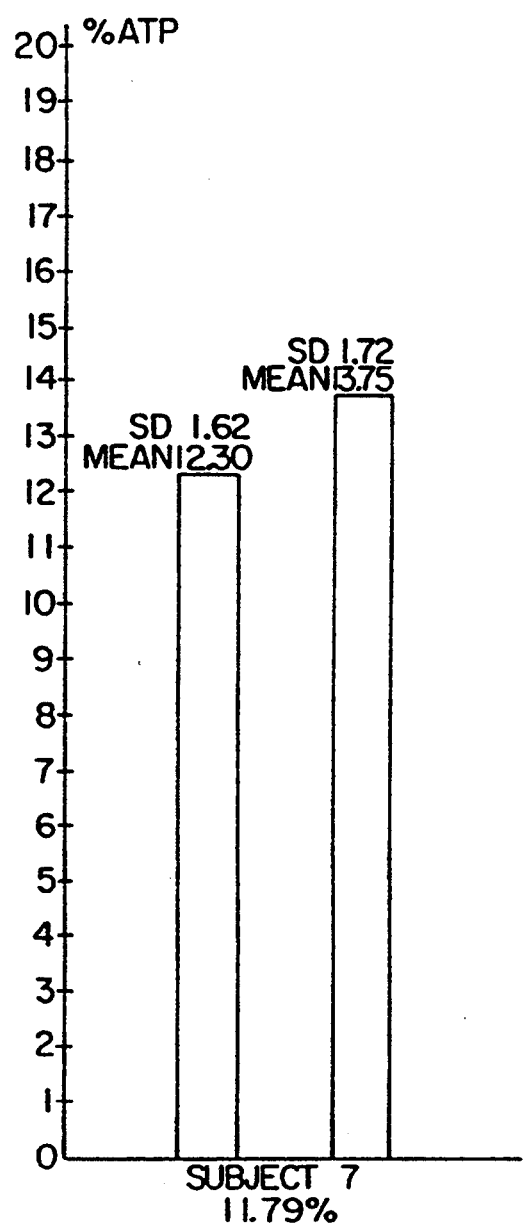
Figure 9:
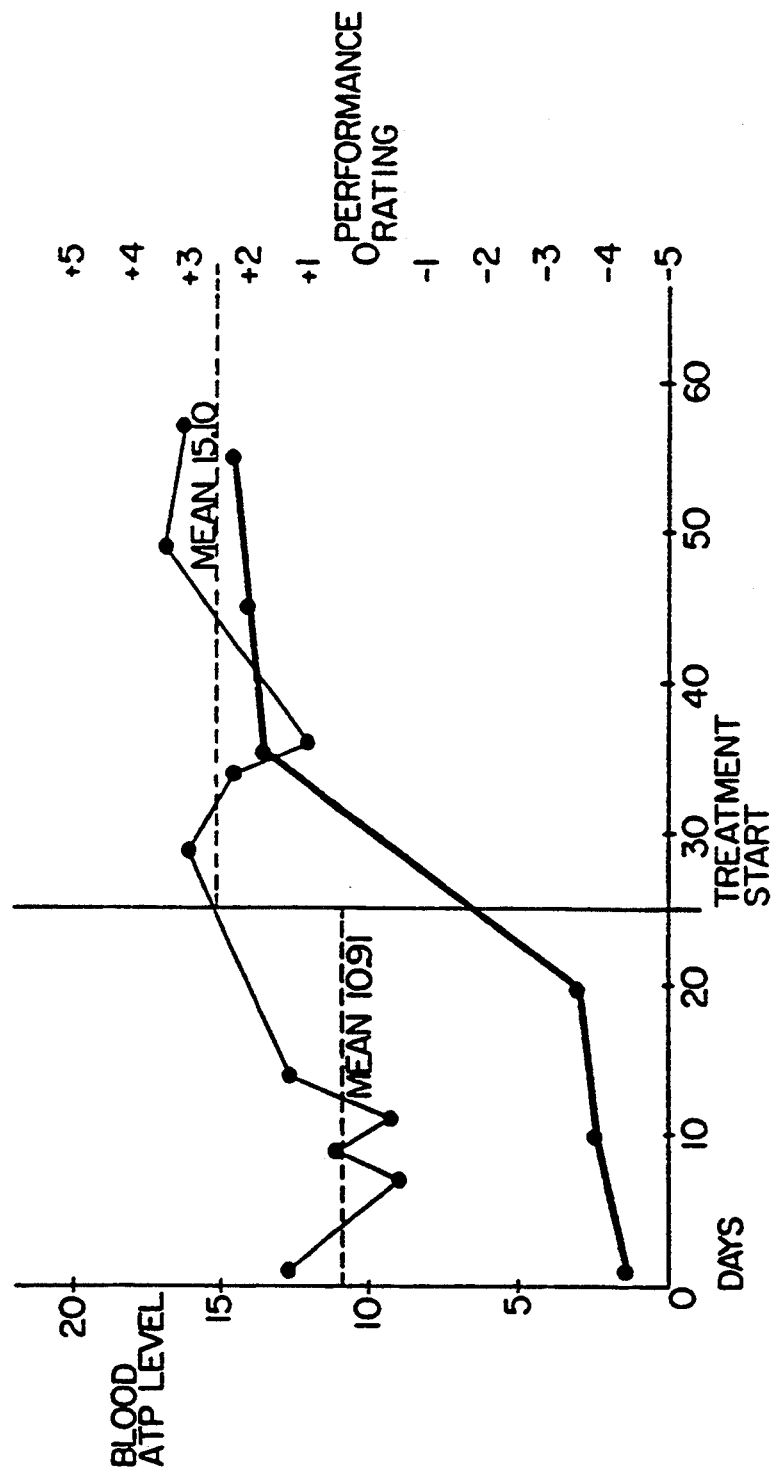
FIGS. 9–12 respectively illustrate the correlation between increased ATP blood levels and increased performance levels for four of the seven subjects.
Figure 10:
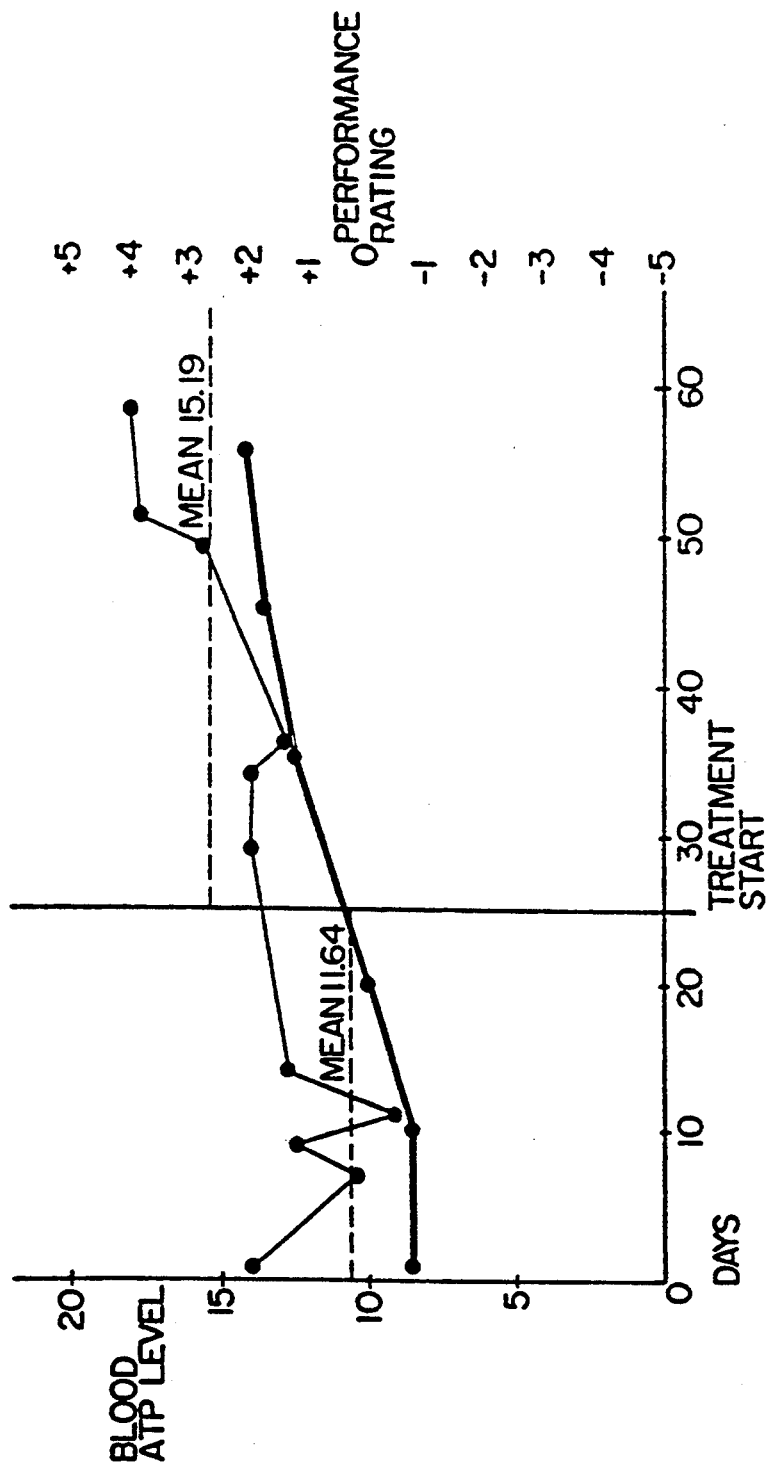
Figure 11:
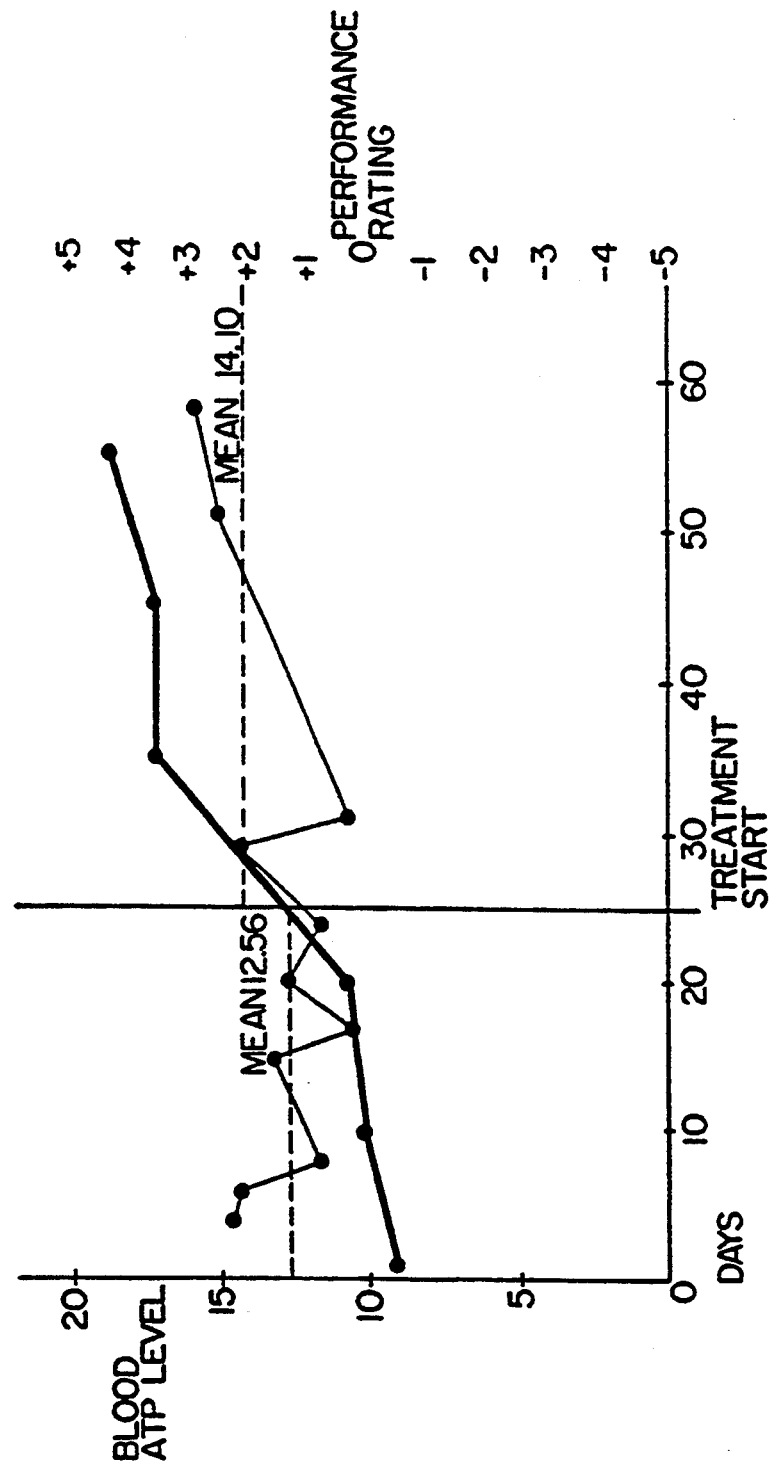
Figure 12:
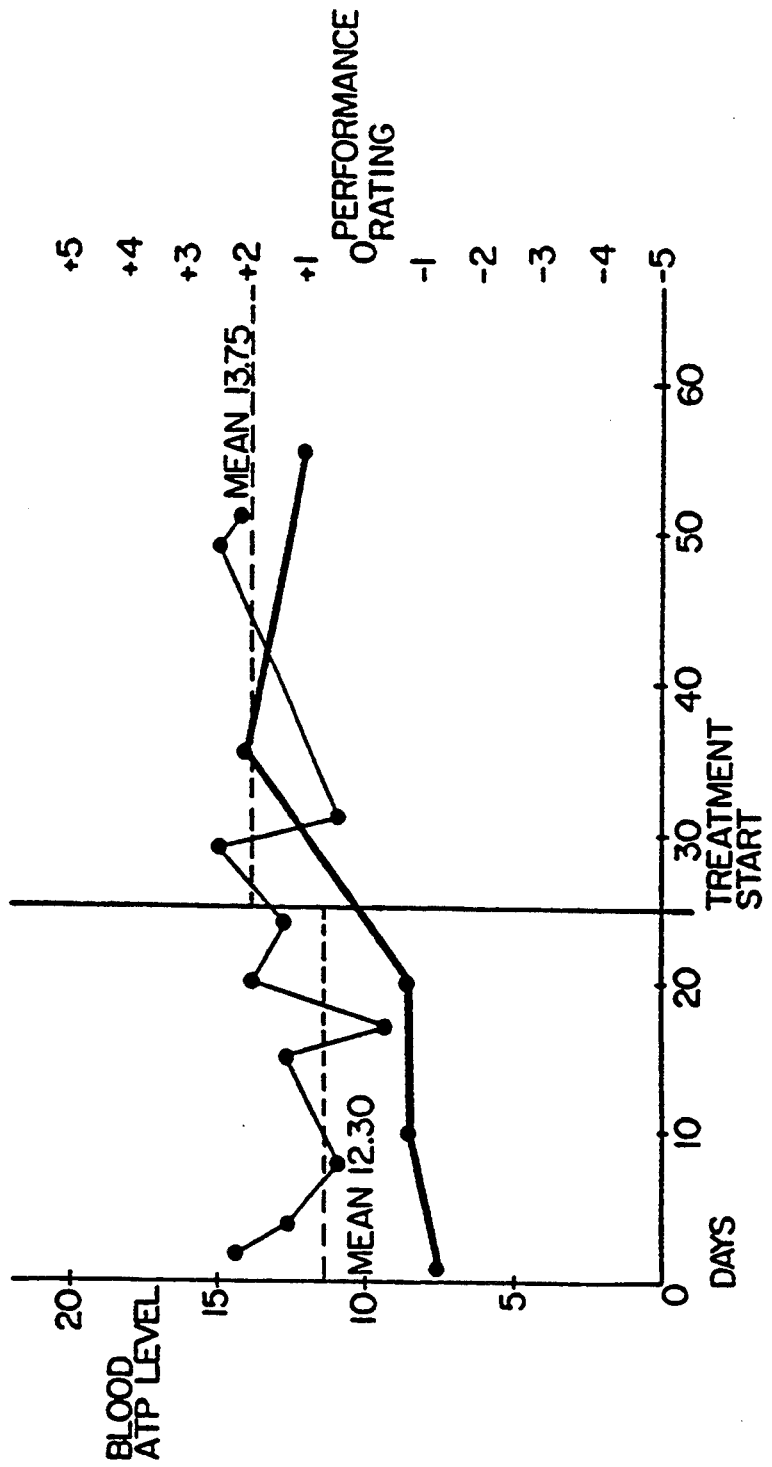

Dietary supplementation with the present invention had a marked effect on the level of ATP in the subjects' blood. As noted above, the blood level of ATP is directly related to the level of ATP inside the cell. FIGS. 1A and 1B illustrate ATP blood levels for all seven subjects before and after dietary supplementation. As a group, after supplementation, subjects had a mean increase (percentage increase) of ATP blood levels of 23.54%. FIGS. 2-8 illustrate that each individual subject showed a marked increase in ATP blood levels ranging from a high of 38.4% (FIG. 2) to a low of 11.8% (FIG. 8).

FIGS. 9-12 illustrate the correlation between increased blood levels of ATP and improved performance level for four of the seven subjects. FIGS. 9-12 correspond to subjects 1, 3, 4 and 7 respectively. Since these four subjects continue to race competitively and train accordingly, they generated sufficient data to form the basis for an ATP blood level/performance level correlation. The solid line on each of the figures illustrates, in alternate form, the data expressed in the bar graphs of FIGS. 1-8. That is, dietary supplementation with the present invention produces a marked increase in ATP blood levels over the levels found in the period immediately preceding the start of supplementation. The broken line on each of FIGS. 9-12 illustrates the mean ATP blood level for the period immediately preceding supplementation and the period of supplementation. The solid double line in each of the FIGS. 9-12 illustrates the correlation between increased blood levels of ATP and increased performance levels.

As noted above, background information for each subject was collected regarding training performance, stamina, race times and results, and general history. The background information was compiled over a period of approximately one year, the period coinciding with the racing season completed prior to the initiation of dietary supplementation with the present invention. The background information consists of quantitative data such as race times, split times and race results. In addition, the background information includes subjective evaluations of the horses by their trainers. The background information collected on each subject was used to establish an average expected behavior or zero rating for each horse. The zero rating was established by evaluating each subject on the basis of four criteria: speed, stamina, aggressiveness and vitality. Each subject was given a rating for each of the four criteria based on a scale of −5 to +5. Once the zero rating for each subject was established, the horses were again evaluated according to the four criteria during the twenty-five day period preceding dietary supplementation and for the period of dietary supplementation. The second and third sets of evaluations resulted in a performance rating relative to the previously determined zero rating for each of the periods just mentioned.

As FIGS. 9-12 clearly illustrate, each of the subjects had a performance level very near to or below their zero rating for the twenty-five day period preceding the initiation of supplementation. However, FIGS. 9-12 also clearly indicate that as ATP blood levels increased during the period of dietary supplementation, performance levels increased to the point where, by the end of the supplementation period, each of the subjects had a performance rating well above the subject's zero rating. In fact, two of the subjects, number 4, a four-year-old, and number 7, a seven-year-old, established new lifetime race marks. It is important to note that at no time during the study were trainers informed of any blood test results.

2. Increased Rate of Wound Repair

To demonstrate that the composition of the present invention increases the rate of wound repair, another series of experiments were conducted wherein the composition was applied to excised wounds on the dorsum of laboratory rats. This was performed as follows: male Sprague-Dawley rats (250-300 g, Charles River Breeding Laboratories, Willmington, Me.) were anesthetized with an intraperitoneal injection of Ketamine/Rompun (90 mg/Ketamine and 10 mg/Rompun). Each rat was given a single full-thickness excised wound 2.5 cm in diameter over the dorsal midline. While the rats were anesthetized, photographs were taken to represent zero time (initial size [area]) compared to a second photograph taken ten days later. For forty-eight hours post-surgery, all animals were maintained on analgesic levels of Acepromazine (0.015%) in their water supply, which eliminated signs of discomfort from the wounds. After the experimental period, the rats were euthanized and skin sections prepared for sub-stage illumination and photographic measurement of final wound area. At this time, the wounded areas were dissected free from surrounding tissue, weighed and frozen in dry ice/acetone for future ATP determination. The process required 45 seconds from the removal of skin section to freezing in a weighing boat for ATP analysis. The procedures used for ATP determination were the same as those outlined above using the Sigma Diagnostic test kit.

The experimental design consisted of eight (8) groups containing six (6) rats each with treatment summarized as follows:

Group 1—composition of the present invention (1% composition in sterile isotonic saline). The most preferred composition is set out in Table III along with the acceptable weight ranges of the individual components.

Group 2—ATP solution (33 mg per ml in sterile isotonic saline).

Group 3—a solution containing both the composition and ATP combined to give the same concentrations above.

Group 4—the composition in a gel (10% Avalon gel containing 1% of the composition).

Group 5—ATP in a gel (10% Avalon gel containing 33 mg per ml added in sterile saline). (Avalon is a tradename for a copolymer gel commercially available from Summit Hill Laboratories, Avalon, N.J.)

Group 6—the composition and ATP combined in 10% Avalon gel to provide the same concentrations as above.

Group 7—sterile isotonic saline in a gel.

Group 8—sterile isotonic saline solution.

TABLE III

Composition of ATP-E

| Component | Preferred Grams | Acceptable Grams |
|---|---|---|
| L-glycine | 8.9 | 8.0–9.8 |
| L-arginine | 35.4 | 31.9–38.9 |
| D/L methionine | 177.2 | 159.5–194.9 |
| Choline chloride | 149.2 | 134.3–164.1 |
| Inositol | 131.5 | 118.3–144.7 |
| L-aspartic acid | 131.5 | 118.3–144.7 |
| L-tryptophan | 38.4 | 34.6–42.2 |
| L-phenylalanine | 31.0 | 27.9–34.1 |
| L-histidine | 29.5 | 26.5–32.4 |
| L-proline | 22.2 | 20.0–24.4 |
| D-ribose | 131.5 | 118.4–144.7 |
| Magnesium phosphate | 113.7 | 102.3–125.1 |
| | 1000.0 | 900.0–1100.0 |

Treatments with the above solutions and gels were administered once daily in the first trial reported here. In the second trial, solutions and gels were applied three times daily for the first three says, then once daily for seven days. Each application consisted of either 0.5 ml of solution or 0.5 g of gel. At the end of the ten day period in both trials, the rats were euthanized and wound tissues taken for study.

The procedure for wound size measurements was as follows: Wound size measurements were made from standardized photographs, and area was determined with a planimeter. The sections were photographed with standardized magnification, and planimetric measurement was made of the wound outline. A metric scale in the plane of the wound assured reproducible determinations.

Figure 13:
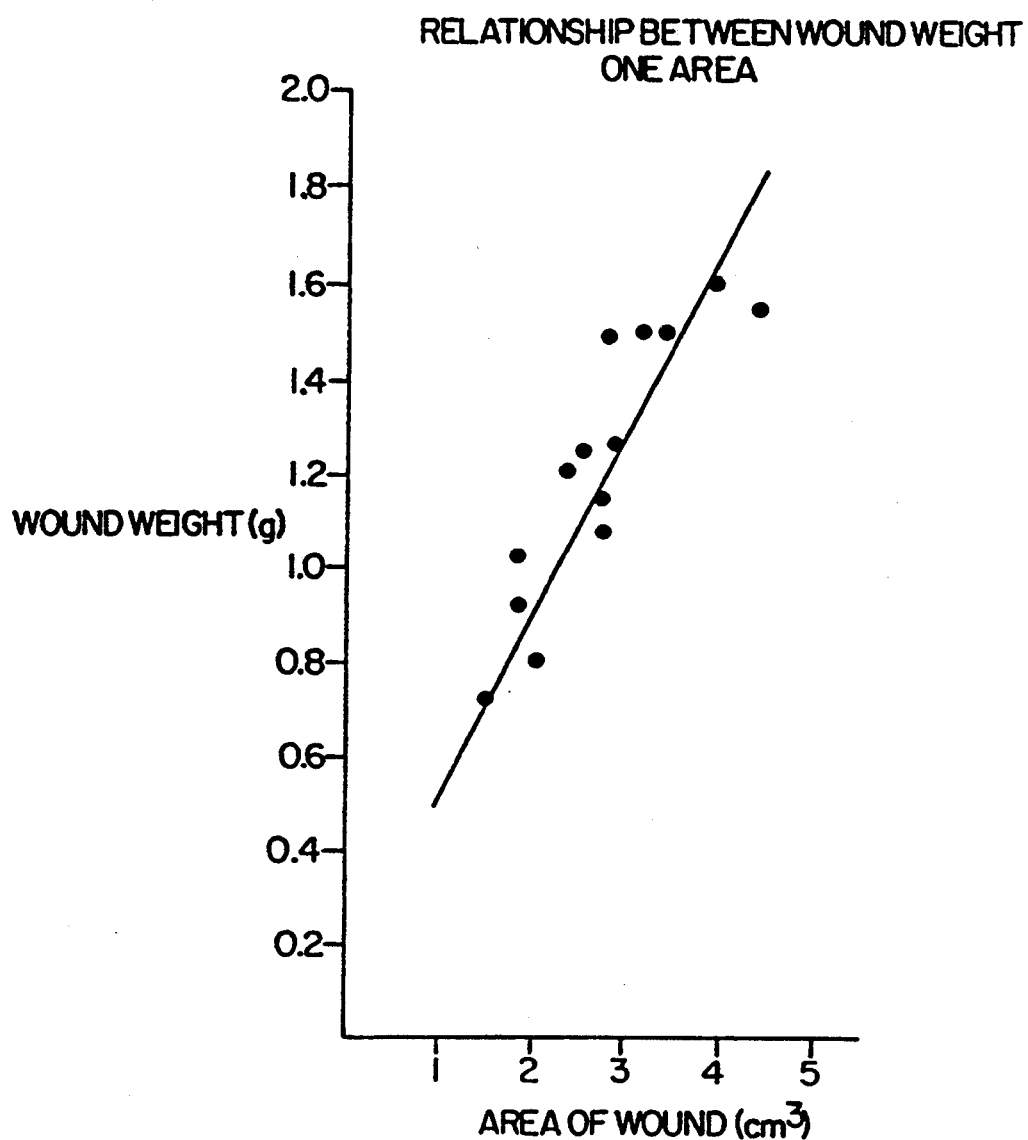
FIG. 13 illustrates the relationship between wound surface area and wound weight in a series of experiments conducted wherein the present invention was applied to excised wounds on the dorsum of laboratory rats.

Wound weights were determined by making an excision of the entire wound down to the panus. FIG. 13 shows the correlation between wound area surface and wound weight, thus providing a basis for determinations on either weight or area.

After each wound was removed it was immediately frozen at −80° C. for wound weight and ATP determination. The concentration of ATP was determined in wound tissue by mincing the entire section containing granulation tissue. The ATP levels were expressed as ATP milligram/10 g of tissue.

The data set out in table IV below demonstrate that a single daily application of the composition as a solution produced a rate of closure which was 17.8% faster then wounds treated with sterile isotonic saline (control). When the composition was applied as a gel, the rate was 1.2% faster. The composition applied three times a day as a solution produced a marked improvement over treatments applied once each day. The data shown in Table V demonstrates these improvements, wherein composition treated wounds had a mean reduction of 37.1%, ATP 31.2% and the mixture composition/ATP 37.3%. The values for percent reduction are based on a decrease in wound weight compared to the mean wound weight of 1.153 for the isotonic saline-treated control wounds.

TABLE IV

Percent Increase in Contraction Rate Over Control When Applied Once Each Day for 10 Days

| Group | Initial | Final | Difference | % Increase Over Control* |
|---|---|---|---|---|
| I | Composition Solution | 59.3 (+12.3) | 77.3 | 17.8 |
| II | ATP Solution | 61.1 (+94) | 69.4 | 5.8 |
| III | Composition Gel | 61.5 (+13.2) | 66.4 | 1.2 |
| IV | ATP Gel | 71.9 (+7.4) | 61.6 | (6) |
| V | Saline Gel Control | 64.3 (+11.5) | 71.3 | — |
| VI | Isotonic Saline Control | 72.3 (+14.4) | 65.6 | — |

Initial values (included in first column): I 136.6 (+7.30); II 130.5 (+12.8); III 127.9 (+6.7); IV 133.5 (+5.8); V 135.6 (+5.5).

*Value for difference (initial minus final) for treated minus that difference for control divided by control times 100 equals percent increase in contraction rate.

TABLE V

Percent Reduction in Wound Weight

| | Wound Weight | Percent Reduction* |
|---|---|---|
| | GROUP I COMPOSITION | |
| 1 | — | — |
| 2 | 0.832 | 27.9 |
| 3 | — | — |
| 4 | 0.627 | 45.6 |
| 5 | 0.706 | 38.7 |
| 6 | 0.736 | 36.2 |
| | | 37.1 ± 7.3 |
| | GROUP II ATP | |
| 1 | 0.765 | 33.7 |
| 2 | 0.855 | 25.9 |
| 3 | 1.053 | 8.7 |
| 4 | 0.614 | 46.8 |
| 5 | 0.838 | 27.4 |
| 6 | 0.642 | 44.4 |
| | | 31.2 ± 13.9 |
| | GROUP III MIXTURE COMPOSITION/ATP | |
| 1 | 0.887 | 23.1 |
| 2 | 0.708 | 38.6 |
| 3 | 0.700 | 39.3 |
| 4 | 0.734 | 36.4 |
| 5 | 0.589 | 48.9 |
| 6 | 0.721 | 37.5 |
| | | 37.3 ± 8.2 |
| | GROUP VIII ISOSALINE CONTROL | |
| | Value used for above calculations was 1.153 ± 0.131 | |
| 1 | 1.270 | |
| 2 | 1.131 | |
| 3 | 0.976 | |
| 4 | 1.234 | |
| 5 | 1.026 | |
| 6 | 1.284 | |

*The control value minus treated value and that difference divided by the control times 100 yields percent reduction.

Figure 14:
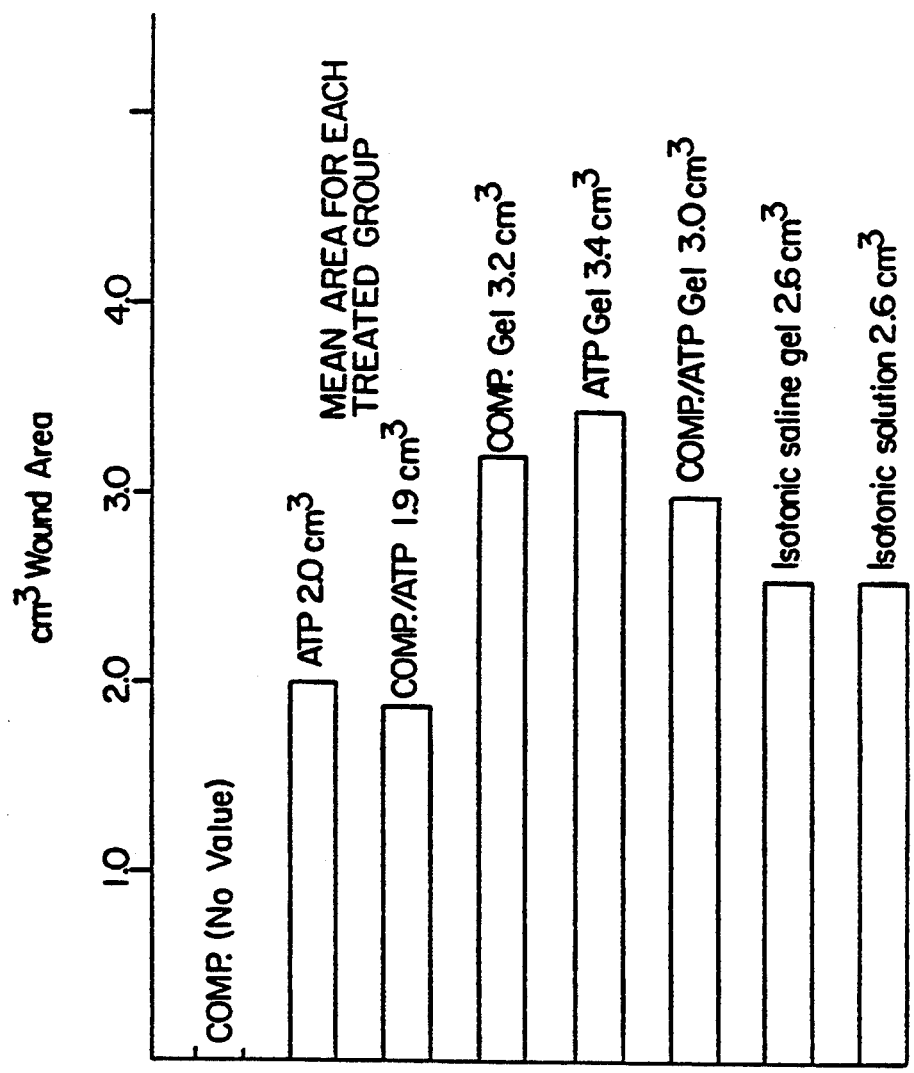
FIG. 14 illustrates the increased rate of wound contraction produced by gels containing the present invention and ATP as compared to a control gel.

FIG. 13 shows the relationship between wound surface area and wound weight. The linear relationship between weight and area suggests that weight measurements may be a useful means for determining wound contraction. The bar graph shown in FIG. 14 depicts the increased rate of contraction for composition/ATP mixture gels compared to control gels. Although the gel treated wounds contracted faster than controls, they did not contract as fast as the solution treated wounds. However, in each group wounds treated with the composition or the composition/ATP mixture had greater rates of contraction than their counterparts.

Figure 15:
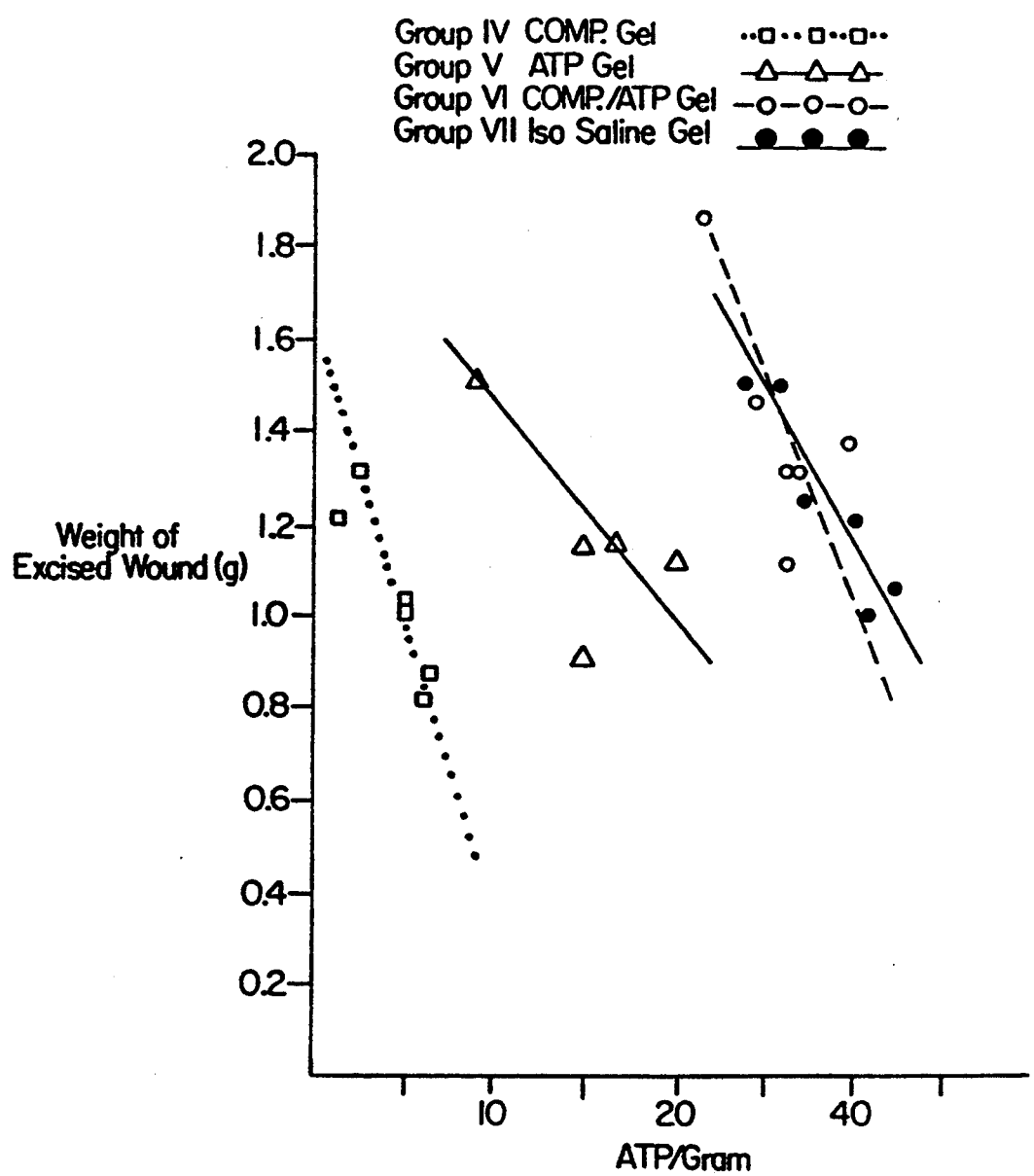
FIGS. 15 and 16 illustrate the relationship between the reduction in wound weight and the amount of ATP found in the wound for gel-treated wounds.
Figure 16:
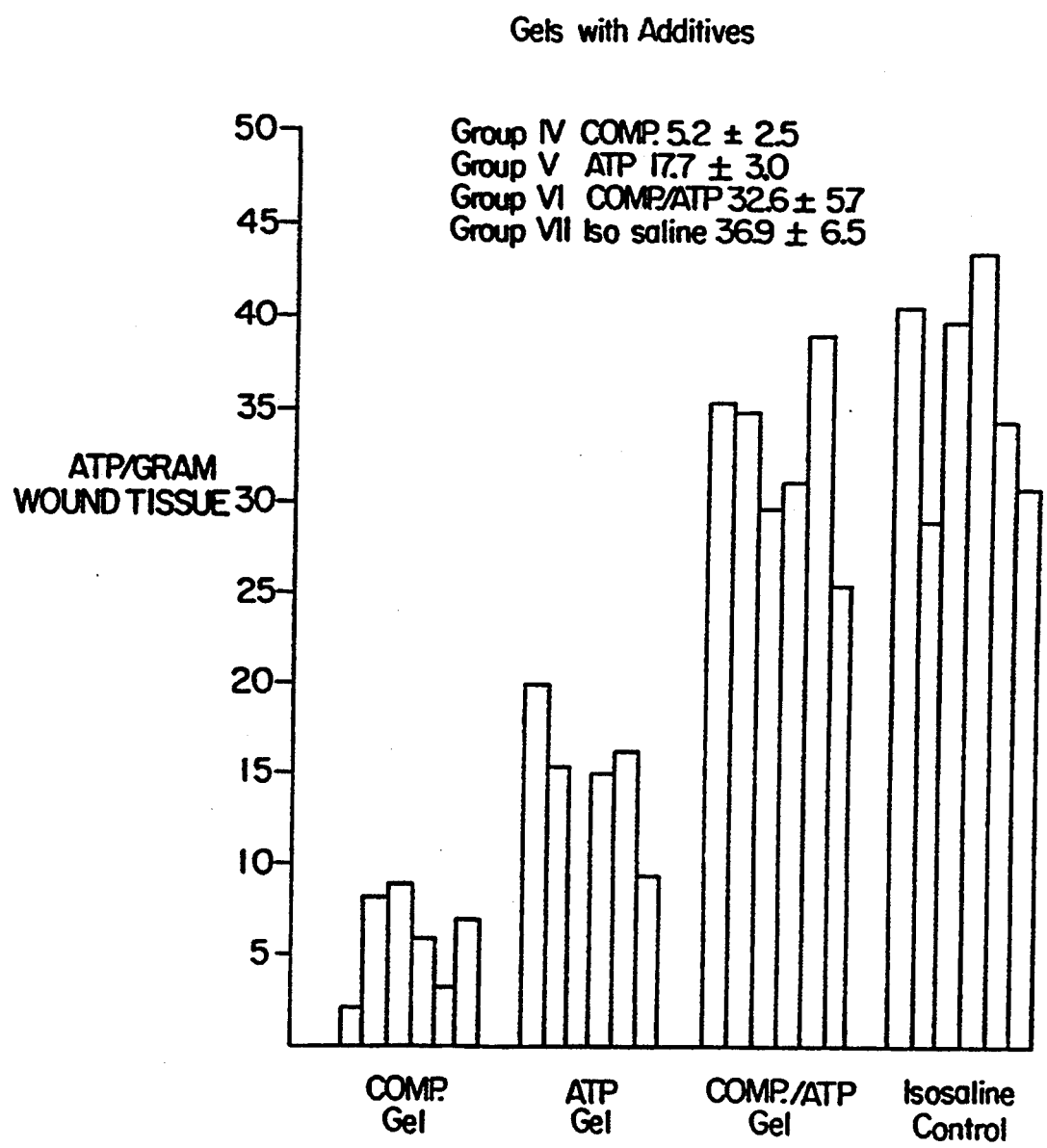

Both solution and gel treatments, in addition to producing a marked reduction in wound weight, also reduced the amount of ATP found in the wound. This is evident in Tables VI and VII and in FIGS. 15 and 16. While it is apparent both in gel and solution treated wounds that ATP levels are reduced by the composition, the reduced level of ATP at the wound site is not unexpected, since protein metabolism for wound repair and the wound contraction produced by the myofibroblasts both require significant amounts of energy in the form of ATP. That is, additional intracellular ATP synthesized by the cells in response to the present invention is quickly utilized for contraction, glueoneogenesis and protein synthesis.

TABLE VI

Solutions Applied to Excised Wounds

| | Wound Wt. | Initial OD | Final OD | ATP | ATP/G | Mean |
|---|---|---|---|---|---|---|
| Group I | | | | | | |
| 1 | -0- | — | — | — | — | |
| 2 | 0.832 | 0.645 | 0.616 | 7.4 | 8.89 | ATP |
| 3 | 1.668 | 0.654 | 0.638 | 6.2 | 3.72 | 8.78 ± 2.57 |
| 4 | 0.627 | 0.654 | 0.631 | 8.0 | 12.8 | Tissue Wt. |
| 5 | 0.706 | 0.671 | 0.638 | 12.9 | 18.3 | 0.725 ± .08 |
| 6 | 0.736 | 0.639 | 0.615 | 9.4 | 12.8 | |
| Group II | | | | | | |
| 1 | 0.765 | 0.454 | 0.420 | 13.3 | 17.4 | |
| 2 | 0.855 | 0.454 | 0.451 | 1.2 | 1.40 | ATP |
| 3 | 1.053 | 0.454 | 0.468 | — | | 8.9 ± 5.37 |
| 4 | 0.614 | 0.418 | 0.427 | — | | Tissue Wt. |
| 5 | 0.838 | 0.418 | 0.450 | 11.7 | 14.0 | 0.794 ± .160 |
| 6 | 0.642 | 0.469 | 0.450 | 7.4 | 14.6 | |
| Group III | | | | | | |
| 1 | 0.887 | 0.631 | 0.591 | 15.6 | 17.6 | |
| 2 | 0.708 | 0.445 | 0.485 | — | | ATP |
| 3 | 0.700 | 0.423 | 0.436 | — | | 6.9 ± 6.18 |
| 4 | 0.734 | 0.423 | 0.417 | 2.3 | 3.1 | Tissue Wt. |
| 5 | 0.589 | 0.423 | 0.405 | 7.0 | 11.9 | 0.723 ± .095 |
| 6 | 0.721 | 0.609 | 0.602 | 2.7 | 3.7 | |
| Group VIII | | | | | | |
| 1 | 1.270 | 0.515 | 0.500 | 5.9 | 4.7 | |
| 2 | 1.131 | 0.474 | 0.468 | 2.3 | 2.0 | ATP |
| 3 | 0.976 | 0.495 | 0.478 | 6.6 | 6.8 | 7.64 ± 4.75 |
| 4 | 1.234 | 0.477 | 0.478 | — | | Tissue Wt. |
| 5 | 1.026 | 0.477 | 0.456 | 8.2 | 8.0 | 1.153 ± 0.131 |
| 6 | 1.284 | 0.670 | 0.631 | 15.2 | 11.8 | |

TABLE VII

Gels Applied to Excised Rat Wounds (Three Applications Per Day)

| | Wound Wt. | Initial OD | Final OD | ATP | ATP/G | Mean |
|---|---|---|---|---|---|---|
| Group IV | | Composition Gel | | | | |
| 1 | 1.218 | 0.553 | 0.549 | 1.6 | 1.3 | |
| 2 | 0.805 | 0.579 | 0.565 | 5.5 | 6.8 | ATP |
| 3 | 0.882 | 0.565 | 0.548 | 6.6 | 7.5 | 5.2 ± 2.5 |
| 4 | 1.139 | 0.565 | 0.548 | 6.6 | 5.8 | Tissue Wt. |
| 5 | 1.376 | 0.580 | 0.570 | 3.9 | 2.8 | 1.082 ± 0.212 |
| 6 | 1.076 | 0.956 | 0.938 | 7.2 | 6.7 | |
| Group V | | | | | | |
| 1 | 1.100 | 0.774 | 0.717 | 22.2 | 20.2 | |
| 2 | .954 | 0.815 | 0.777 | 14.8 | 15.5 | ATP |
| 3 | 1.236 | 0.906 | 0.588 | 124.0 | 100.3 | 17.7 ± 3.0 |
| 4 | 1.158 | 0.749 | 0.704 | 17.6 | 15.2 | Tissue Wt. |
| 5 | 1.157 | 0.929 | 0.881 | 18.7 | 16.2 | 1.196 ± 0.207 |
| 6 | 1.574 | 0.608 | 0.569 | 15.2 | 9.7 | |
| Group VI | | Mixture Composition/ATP Gel | | | | |
| 1 | 1.336 | 0.580 | 0.458 | 47.6 | 35.6 | |
| 2 | 1.111 | 0.598 | 0.498 | 39.0 | 35.1 | ATP |
| 3 | 1.480 | 0.592 | 0.479 | 44.1 | 29.8 | 32.6 ± 5.7 |
| 4 | 1.338 | 0.678 | 0.568 | 42.9 | 32.1 | Tissue Wt. |
| 5 | 1.390 | 0.595 | 0.453 | 55.4 | 39.9 | 1.425 ± 0.260 |
| 6 | 1.896 | 0.595 | 0.482 | 44.1 | 23.3 | |
| Group VII | | Isosaline Gel Control | | | | |
| 1 | 1.073 | 0.635 | 0.520 | 44.9 | 41.8 | |

TABLE VII-continued

Gels Applied to Excised Rat Wounds (Three Applications Per Day)

| | Wound Wt. | Initial OD | Final OD | ATP | ATP/G | Mean |
|---|---|---|---|---|---|---|
| 2 | 1.540 | 0.628 | 0.520 | 42.1 | 27.3 | ATP |
| 3 | 1.219 | 0.604 | 0.476 | 49.9 | 40.9 | 36.9 ± 6.5 |
| 4 | 1.127 | 0.604 | 0.476 | 49.9 | 44.3 | Tissue Wt. |
| 5 | 1.256 | 0.577 | 0.465 | 43.7 | 34.8 | 1.285 ± 0.192 |
| 6 | 1.496 | 0.617 | 0.494 | 48.0 | 32.1 | |

In summary, topical formulations including solutions and gels containing the compositions of the present invention caused an improvement in wound closure rate over that of controls consisting of sterile isotonic saline. The wound repair rate appeared dose-dependent in reference to the number of applications made; that is, one application daily produced a 17.8% faster rate of wound closure and three applications per day produced a 37.2% faster rate. As in any other bioassay, dose-related responses are significant from the standpoint of data validity. Composition containing solutions and gels caused an improved wound closure rate over that of controls by increasing the available components for gluconeogenesis and protein synthesis. In addition, increased intracellular ATP synthesized by the cells in response to the present invention was quickly utilized as an energy source for these processes and for the wound contraction mechanism. Finally, the stoichiometry of wound weight to wound size was consistent as was the inverse relationship between wound weight and ATP levels.

It should be noted that the ingredients recited in Table III are not all essential in formulating wound healing compositions in accordance with the invention. Again, any amino acid (or amino acids) which is (are) an ATP precursor (or precursors) could be employed. At least one of choline or inositol can be used as the metabolite or carnitine can be added or substituted. Finally, any electrolyte could be used in the composition to be applied topically (or supplied to the wound systemically, e.g. by oral or parenteral administration). It is preferable that a source of phosphate ion be included most preferably along with a source of magnesium and/or manganese ion. Finally, to the extent methionine is used, which is preferred, it is preferable that at least one of glycine, serine or retinol be used along with methionine. Although, in the wound-healing use, the present composition is preferably administered topically, excess levels of methionine unaccompanied by glycine or its substitutes are expected to have an inhibitory effect on angiogenesis and/or other tissue repair processes. Preferred compositions contain 2.5–4.5 millimolar methionine regardless of whether they also contain other amino acids for the purpose of synthesizing ATP. In addition, methionine containing compositions also preferably include an equimolar amount of glycine and/or retinol and/or serine. Such compositions can be formulated in solution or semisolid form using such excipients, vehicles and diluents as are well-known in the art of topical pharmaceutical formulations. Finally, for wound healing compositions in accordance with the present invention, which also contain all or some of the ATP synthesis ingredients, the same relative amounts can be used as disclosed above for the orally administered compositions.

Another advantage of the present invention is the fact that the topical application of compositions according to the invention have an antimicrobial effect which helps prevent or abate infection in a wound. In fact, the antimicrobial effect of the present invention is expected to accelerate wound closure even without increasing the level of ATP synthesized (and consumed) at the locus of a wound. The antimicrobial effect will be demonstrated as follows:

Several groups of CD-1 male mice (Charles River Laboratory, Wilmington, Mass.) not previously exposed to P.aeruginosa will be anaesthetized. A full-thickness excised wound (1 cm$^2$) will be prepared over their midline. A 24-hour culture of P.aeruginosa will be used to infect wounds (approximately $5 \times 10^{10}$ viable organisms or 10-fold dilutions will be placed in each wound) except for negative controls. One hour after infection, all experimental infected groups will be treated by topical application of (a) ATP-E (per Table III) except that magnesium chloride and potassium phosphate will be substituted for magnesium phosphate in solution as described in the wound-healing experiments disclosed above (one group); (b) ATP-E per Table III but containing no methionine (one group); (c) methionine alone (one group) in an amount equivalent to that contained in ATP-E; (d) methionine alone in $3 \times$ the ATP-E amount, i.e. about 0.05 g methionine/cc of isotonic saline; (e) methionine plus at least one of glycine, retinol and serine in amounts within the range from about 2.5 mmoles to about 4.5 mM of methionine and equimolar amounts of serine, glycine and/or retinol; (f) methionine and glycine above in the same amounts as (e); (g) ATP-E depleted of magnesium and phosphate; and (h) ATP-E depleted of inositol and choline. The uninfected controls will receive isotonic saline and the positive uninfected controls will receive the aforementioned compositions. The infected controls will receive isotonic saline. A standard curve will be made using dilutions of P. aeruginosa and measuring length of time till death of mice (latency curve) as described in Kenyon, A. J. et al, *Am. J. Vet. Res.* 47:1101–1104, 1986 hereby incorporated by reference in its entirety. The details of these experiments will also be performed according to the reference. ATP-E and the other compositions will be applied at least once for these experiments (although the preferred therapeutic regimen is one to three applications per day for at least one day preferably until wound closure is complete). The ability of the mice to survive infection will be used to measure the antimicrobial effect of the compositions. Wound size and weight measurements will be used to assess the wound healing effect as described above in infected and in not infected wounds. If desired, wound breaking strength can also be measured, as is known in the art, for example, using the procedure of Crawford, D. T. et al, *J. Surg.. Res.*, 5:265–269, 1965, incorporated entirely by reference. Non infected wounds should be evaluated to determine whether the amount of wound repair is due solely to antimicrobial action. This can be accomplished by histologic examination of wounds as disclosed in Kenyon, A. J., et al, *Controlled Wound Repair in Guinea Pigs Using Antimicrobials that Alter Fibroplasia*, Am. J. Vet. Res. 47:96–101, 1986, which is also entirely incorporated by reference.

It is anticipated that the compositions of the present invention, especially those containing methionine will accelerate wound healing while also exerting an antimicrobial effect. As is known, many antimicrobial agents have a depressant effect on at least one of angiogenesis fibroplasia and glueoneogenesis. It is anticipated that the present invention will increase the rate of wound repair in addition to having an antimicrobial effect.

We claim:

1. A composition of matter for increasing the intracellular level of ATP comprising:
   at least one amino acid selected from the group consisting of amino acid metabolic precursors of ATP and mixtures thereof;
   at least one metabolite selected from the group consisting of choline, inositol and carnitine; and
   a compound selected from the group consisting of ribose, and saccharides and polysaccharides which upon hydrolysis or metabolization yield ribose, and mixtures of such compounds.

2. The composition of claim 1 wherein said precursors are L-glycine, L-arginine, D/L methionine, L-aspartic acid, L-tryptophan, L-phenylalanine, L-histidine and L-proline and combinations thereof.

3. The composition of claim 1 wherein the metabolite is selected from the group consisting of choline chloride and in-ositol.

4. The composition of claim 1 further comprising an electrolyte which comprises at least one of a source of phosphate ion and a source of at least one of magnesium ion and manganese ion.

5. The composition of claim 4 wherein the electrolyte comprises a source of magnesium ion.

6. The composition of claim 1 wherein said amino acid includes methionine in an amount at least 15% by weight of said composition, said composition also comprising at least one of glycine, serine and retinol in an amount sufficient to suppress toxic effects of said methionine.

7. A composition of matter for increasing the intracellular level of ATP comprising an electrolyte, at least one amino acid selected from the group consisting of amino acid metabolic precursors of ATP and mixtures thereof and at least one metabolite selected from the group consisting of inositol and choline.

8. A composition of matter for increasing the intracellular level of ATP comprising at least one electrolyte, at least one amino acid selected from the group consisting of amino acid metabolic precursors of ATP and mixtures thereof; and
   at least one compound selected from the group consisting of ribose, and saccharides and polysaccharides which upon hydrolysis or metabolization yield ribose.

9. The composition of any one of claims 1, 4, 6, 7 and 8 further comprising vitamins, minerals and flavoring agents.

10. The composition of claim 7 or 8 wherein the electrolyte comprises a source of magnesium or manganese ion and a source of phosphate ion in the form of physiologically acceptable salts.

11. A method for increasing intracellular levels of ATP comprising delivering to the skeletal muscles of a mammal in the presence of an electrolyte:
    at least one amino acid selected from the group consisting of amino acid metabolic precursors of ATP and mixtures thereof;
    at least one metabolite selected from the group consisting of choline and inositol and carnitine; and
    a compound selected from the group consisting of ribose, and saccharides and polysaccharides which upon hydrolysis or metabolization yield ribose and mixtures of such compounds.

12. A method for increasing intracellular levels of ATP comprising delivering to the skeletal muscles of a mammal in the presence of ribose:
- at least one amino acid selected from the group consisting of amino acid metabolic precursors of ATP and mixtures thereof;
- at least one metabolite selected from the group consisting of choline, inositol and L-carnitine; and
- an electrolyte.

13. A method for increasing intracellular levels of ATP comprising delivering to the skeletal muscles of a mammal in the presence of at least one metabolite selected from the group consisting of choline, inositol and carnitine:
- at least one amino acid selected from the group consisting of amino acid metabolic precursors of ATP and mixtures thereof; and
- a compound selected from the group consisting of ribose, and saccharides and polysaccharides which upon hydrolysis or metabolization yield ribose and mixtures of such compounds.

14. The method of claim 11, 12 or 13, wherein said delivery is accomplished by oral route.

15. An antimicrobial composition for topical wound treatment comprising:
(a) methionine in an antimicrobially effective amount;
(b) at least one of glycine, serine and retinol in an amount sufficient to substantially prevent or counteract the toxicity of methionine; and
(c) a pharmaceutically acceptable topical vehicle or diluent.

16. A method for increasing the rate of wound repair comprising:
delivering to the wound:
- at least one amino acid selected from the group consisting of amino acid metabolic precursors of ATP and mixtures thereof;
- at least one metabolite selected from the group consisting of choline, carnitine and inositol; and
- a compound selected from the group consisting of ribose, and saccharides and polysaccharides which upon hydrolysis or metabolization yield ribose; and
also delivering to said wound (i) methionine in an amount sufficient to have an antimicrobial effect, and (ii) at least one amino acid selected from the group consisting of glycine, serine and retinol in an amount sufficient to substantially prevent or counteract the toxic effects of methionine.

17. A method for increasing the rate of wound repair comprising topically applying to the wound:
a composition comprising methionine in an amount sufficient to exert antimicrobial activity and a physiologically acceptable vehicle or diluent.

* * * * *